US007993843B2

(12) United States Patent (10) Patent No.: US 7,993,843 B2
Cramer et al. (45) Date of Patent: Aug. 9, 2011

(54) GENETIC POLYMORPHISMS IN THE PROSTATE-SPECIFIC ANTIGEN GENE PROMOTER

(75) Inventors: Scott D. Cramer, Winston-Salem, NC (US); Anuradha Rao, Winston-Salem, NC (US); Jianfeng Xu, Clemmons, NC (US); Bao-li Chang, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 12/720,818

(22) Filed: Mar. 10, 2010

(65) Prior Publication Data

US 2010/0330566 A1 Dec. 30, 2010

Related U.S. Application Data

(60) Division of application No. 11/846,127, filed on Aug. 28, 2007, now Pat. No. 7,718,372, which is a continuation of application No. 10/740,662, filed on Dec. 19, 2003, now abandoned.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ......... 435/6; 435/91.2; 536/23.1; 536/24.1; 536/24.31

(58) Field of Classification Search ........................ None
See application file for complete search history.

(56) References Cited

U.S. PATENT DOCUMENTS 6,740,516 B2   5/2004   Savitzky et al.

OTHER PUBLICATIONS

Halushka MK et al. Patterns of single-nucleotide polymorphisms in candidate genes for blood-pressure homeostasis. Nature Genetics. Jul. 1999; 22: 239-247.
NCBI SNP Database ss1362402. National Center for Biotechnology Information, National Library of Medicine, NIH (Bethesda, MD, USA), rs925013, Sep. 6, 2000.
Cicek MS et al. Role of androgen metabolisms genes CYP1B1, PSA/KLK3, and CYP11(alpha) in prostate cancer risk and aggressiveness. Cancer Epidemiology Biomarkers & Prevention. Sep. 2005; 14(9): 2173-2177.
Cramer S D et al. Association between genetic polymorphisms in the prostate-specific antigen gene promoter and serum prostate-specific antigen levels. Journal of the National Cancer Institute. Jul. 2003 95: 1044-1053.
Beebe-Dimmer J L et al. Polymorphisms in the prostate-specific antigen gene promoter do not predict serum prostate-specific antigen levels in African-American men. Prostate Cancer and Prostatic Diseases. 2006. 9: 50-55.
Cleutjens et al., "Two Androgen Response Regions Cooperate in Steroid Hormone Regulated Activity of the Prostate-Specific Antigen Promoter," *J. Biol. Chem.*, 271:6379-6388 (1996).
Cleutjens et al., "An Androgen Response Element in a Far Upstream Enhancer Region is Essential for High, Androgen-Regulated Activity of the Prostate-Specific Antigen Promoter," *Molec. Endocrinol*, 11:148-161 (1997).
Huang et al., "Cooperative Assembly of Androgen Receptor Into a Nucleoprotein Complex That Regulates the Prostate-Specific Antigen Enhancer," *J. Biol. Chem.*, 274:25756-25768 (1999).
Medieros et al., "Linkage Between Polymorphisms in the Prostate-Specific Antigen AREI Gene Region, Prostate Cancer Risk, and Circulating Tumor Cells," *Prostate* 53:88-94 (2002).
Rao et al., "Identification of a Polymorphism in the ARE I Region of the PSA Promoter," *Proc. Amer. Assn. Cancer Res.* 40:60 (1999).
Rao et al., "Analysis of the G/A Polymorphisms in the Androgen Response Element I of the PSA Gene and Its Interactions with the Androgen Receptor Polymorphisms," *Urology*, 61:864-869 (2002).
Schuur rt al., "Prostate-Specific Antigen Expression is Regulated by an Upstream Enchancer," *J. Biol. Chem.* 7043-7051 (1996).
Sensabaugh, "Isolation and Characterization of a Semen-Specific Protein From Human Seminal Plasma: A Potential New Marker for Semen Identification," *J. Forensic Sci.*, 23:106 (1978).
Sinha et al., "Immunoelectron Microscopic Localization of Prostate-Specific Antigen in Human Prostate by the Protein A-Gold Complex," *Cancer*, 60:1288-1293 (1987).
Stamey et al., "Prostate-Specific Antigen Serum Marker for Andenocarcinoma of the Prostate," *N. Engl. J. Med.*, 317:909-916 (1987).
Stamey et al., "Prostate Specific Antigen in the Diagnosis and Treatment of Adenocarcinoma of the Prostate. Untreated Patients," *J. Urology*, 141:1070-1075 (1989).
Xu et al., "Association Studies of Serum Prostate-Specific Antigen Genes," *Cancer Epidemiol. Biomarkers Prev.* 11:664-669 (2002).
Xue et al., "Genetic Determinants of Serum Prostate-Specific Antigen Levels in Healthy Men From a Multiethnic Cohort," *Cancer Epidemiol Biomark Prev.* 10:575-579 (2001).
Xue et al., Susceptibility to Prostate Cancer: Interaction Between Genotypes at the Androgen Receptor and Prostate-specific Antigen Loci, *Cancer Res.*,60:839-841 (2000).
Zhang et al., "Defining a Functional Androgen Responsive Element in the 5' Far Upstream Flanking Region of the Prostate Specific Antigen Gene," *Biochem. Biophy. Res. Comm.*, 23:784-788 (1997).
Zhang et al., "Identification of Two Novel CIS-Elements in the Promoter of Prostate-Specific Antigen Gene That are Required to Enhance Androgen Receptor-Mediated Transactivation," *Nucleic Acids. Res.*, 25:3143-3150 (1997).

*Primary Examiner* — Carla Myers

(74) *Attorney, Agent, or Firm* — Myers Bigel Sibley & Sajovec, P.A.

(57) ABSTRACT

The present invention includes methods of identifying a subject at risk for increased cellular PSA production and/or prostate cancer by detecting the presence or absence of a genetic polymorphism in the prostate specific antigen gene.

30 Claims, 4 Drawing Sheets

SEQUENCE LISTING

<160> NUMBER OF SEQ ID NOS: 10

<210> SEQ ID NO 1
<211> LENGTH: 19

```
<212> TYPE: DNA
<213> ORGANISM: Artificial
<220> FEATURE:
<223> OTHER INFORMATION: Primer

<400> SEQUENCE: 1
tttggcagtg gagtgctgc                                           19

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
gctttggaat atccctgcca g                                        21

<210> SEQ ID NO 3
<211> LENGTH: 35
<212> TYPE: DNA
<213> ORGANISM: Artificial
<220> FEATURE:
<223> OTHER INFORMATION: Primer

<400> SEQUENCE: 3
atgaattcgt cgaccacagt gtaatgccat ccagg                         35

<210> SEQ ID NO 4
<211> LENGTH: 29
<212> TYPE: DNA
<213> ORGANISM: Artificial
<220> FEATURE:
<223> OTHER INFORMATION: Primer

<400> SEQUENCE: 4
ataggatcca gactgtcctg cagacaagg                                29

<210> SEQ ID NO 5
<211> LENGTH: 18
<212> TYPE: DNA
<213> ORGANISM: Artificial
<220> FEATURE:
<223> OTHER INFORMATION: Primer

<400> SEQUENCE: 5
ccttcaggtg aacaaagg                                            18

<210> SEQ ID NO 6
<211> LENGTH: 18
<212> TYPE: DNA
<213> ORGANISM: Artificial
<220> FEATURE:
<223> OTHER INFORMATION: Primer

<400> SEQUENCE: 6
agaccaggga cactctgg                                            18

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
tcacattagt acaccttgcc c                                        21
```

```
<210> SEQ ID NO 8
<211> LENGTH: 19
<212> TYPE: DNA
<213> ORGANISM: Artificial
<220> FEATURE:
<223> OTHER INFORMATION: Primer

<400> SEQUENCE: 8
tagactgctc tggtcaccc                                              19

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
ggacagggac atcaggcc                                               18

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
gctttggaat atcctgccag                                             20
```

GENETIC POLYMORPHISMS IN THE PROSTATE-SPECIFIC ANTIGEN GENE PROMOTER

RELATED APPLICATIONS

This application claims priority to and is a divisional of U.S. patent application Ser. No. 11/846,127, filed Aug. 28, 2007, now U.S. Pat. No. 7,718,372, which is a continuation of U.S. patent application Ser. No. 10/740,662, filed Dec. 19, 2003, abandoned, the disclosure of each of which is incorporated by reference herein in its entirety.

FIELD OF THE INVENTION

The present invention relates to methods of detecting mutations in the prostate specific antigen gene. More specifically, the present invention relates to methods of detection of a genetic predisposition for increased cellular PSA production and/or prostate cancer.

BACKGROUND OF INVENTION

Prostate specific antigen (PSA) is an androgen-regulated serine protease produced by secretory epithelial cells lining the lumen of normal prostatic glands and the majority of prostate cancers. Sensabaugh, Isolation and characterization of a semen-specific protein from human seminal plasma: A potential new marker for semen identification. *J Forensic Sci* 1978; 23:106; Sinha et al., Immunoelectron microscopic localization of prostate-specific antigen in human prostate by the protein A-gold complex. *Cancer* 1987; 60:1288-93; Stamey et al., Prostate-specific antigen as a serum marker for andenocarcinoma of the prostate. *N Engl J Med* 1987; 317:909-16. The prostate is the major source of PSA. Sensabaugh; Stamey et al.; Hara et al., Immunochemical characteristics of human specific component "γ-Sm". *Nippon Hoigaku Zasshi* 1969; 23:333; Stamey et al., Prostate specific antigen in the diagnosis and treatment of adenocarcinoma of the prostate. Untreated patients. *J Urology* 1989; 141:1070-5. Because of the prostate specificity of PSA expression it has become the most widely used marker for prostate cancer screening and response to therapeutic intervention. Many clinicians consider a serum PSA concentration greater than 4 ng/ml to be abnormal and recommend further screening by needle biopsy upon such a finding. However, PSA testing has a low sensitivity and specificity for detecting prostate cancer. Factors that can contribute to this low sensitivity and specificity include the presence of any non-cancerous prostatic disease (i.e. prostatitis or benign prostatic hyperplasia), age, and race.

There are three androgen response elements that are defined in the PSA promoter. Androgen response element (ARE) I and ARE II are located in the proximal PSA promoter centered at −170 bp and −394 bp from the transcription start site respectively. Xue et al., Genetic determinants of serum prostate-specific antigen levels in healthy men from a multi-ethnic cohort. *Cancer Epidemiol Biomark Prev* 2001; 10:575-9. The androgen response element (ARE) I is a high affinity ARE in the PSA gene. Cleutjens et al., Two androgen response regions cooperate in steroid hormone regulated activity of the prostate-specific antigen promoter. J Biol Chem 1996; 271:6379-88. Recently, genetic polymorphism in ARE I has been reported to be associated with PSA levels. Xue et al., *Cancer Epidemiol Biomark Prev* 2001. This polymorphism is a G/A change at position −158 in the PSA gene, with approximately 50:50 ratios for the two alleles in Caucasians. Rao et al., Identification of a polymorphism in the ARE I region of the PSA promoter. *Proc Amer Assn Cancer Res* 1999; 40:60. It was demonstrated that an association of the A allele occurs with increased serum PSA in healthy men. Cleutjens et al. This polymorphism has also been associated with increased risk for the development of prostate cancer. Xue et al., Susceptibility to prostate cancer: interaction between genotypes at the androgen receptor and prostate-specific antigen loci. *Cancer Res* 2000; 60:839-41; Medieros et al., Linkage between polymorphisms in the prostate specific antigen AREI gene region, prostate cancer risk, and circulating tumor cells. *Prostate* 2002; 53:88-94. Recent studies evaluated the association of this polymorphism with serum PSA in two separate study groups of men without prostate cancer and found no associations. Xu et al., Association studies of serum prostate-specific antigen levels and the genetic polymorphisms at the androgen receptor and prostate-specific antigen genes. *Cancer Epidemiol Biomarkers Prev* 2002; 11:664-9; Rao et al., Analysis of the G/A polymorphism in the androgen response element I of the PSA gene and its interactions with the androgen receptor polymorphisms. *Urology* 2002; 61:864-69.

ARE III is located in the 5' upstream enhancer region centered at −4200. Cleutjens et al., An androgen response element in a far upstream enhancer region is essential for high, androgen-regulated activity of the prostate-specific antigen promoter. *Molec Endocrinol* 1997; 11:148-61; Schuur et al., Prostate-specific antigen expression is regulated by an upstream enhancer. *J Biol Chem* 1996:7043-51; ARE I and ARE III have been shown to have a high affinity for the androgen receptor, while ARE II is a low affinity ARE; Xue et al., *Cancer Epidemiol Biomark Prev* 2001; Huang et al., Cooperative assembly of androgen receptor into a nucleoprotein complex that regulates the prostate-specific antigen enhancer. *J Biol Chem* 1999; 274:25756-68; Schuur et al., Prostate-specific antigen expression is regulated by an upstream enhancer. *J Biol Chem* 1996:7043-51; Pang et al., Prostate tissue specificity of the prostate-specific antigen promoter isolated from a patient with prostate cancer. *Hum Gene Therapy* 1995; 6:1417-26; Zhang et al., Defining a functional androgen responsive element in the 5' far upstream flanking region of the prostate-specific antigen gene. *Biochem Biophys Res Comm* 1997; 231:784-8; and Zhang et al., Identification of two novel cis-elements in the promoter of the prostate-specific antigen gene that are required to enhance androgen receptor-mediated transactivation. *Nucleic Acids Res* 1997; 25:3143-50. Recent data demonstrates the presence of multiple high, medium, and low affinity AREs located in the upstream enhancer region between −3870 and −4366 of the PSA promoter. Huang et al. Few reports have evaluated the contributions of sequences 5' to −5322 of the PSA gene. This is due largely to the presence of a unique Xba I restriction site at this location that is useful for cloning promoter constructs. Thus, it could be beneficial to locate previously unrecognized functional region of the PSA gene that contains polymorphisms with a significant impact on serum PSA in healthy men.

SUMMARY OF INVENTION

The present invention includes methods of identifying a subject at risk for a genetic predisposition for increased cellular PSA production, comprising detecting the presence or absence of a mutation at position 4643, 5412 and 5429 of the prostate specific antigene gene promoter in the subject; and determining that the subject is at an increased risk of a genetic predisposition for increased cellular PSA production due to the presence or absence of the mutation in the prostate specific antigene gene promoter.

The present invention also includes methods of diagnosing prostate cancer or a genetic predisposition for developing prostate cancer in a human subject by providing a biological sample from the subject wherein the sample encodes a promoter of the prostate specific antigen, detecting one or more mutations in the biological sample, and determining that the subject has at least one detected mutation in each genomic copy of the biological sample encoding the promoter of the prostate specific antigen, wherein the presence of at least one detected mutation in each copy of the sequence encoding the promoter of the prostate specific antigen is diagnostic for prostate cancer or a genetic predisposition for developing prostate cancer in the subject, and wherein the mutation occurs at position 4643, 5307, 5412 or 5429 in the promoter of the prostate specific antigen gene.

The present invention also includes methods of identifying a subject with increased prostate serum level comprising detecting the presence or absence of a mutation at position 4643, 5307, 5412 and 5429.

Additionally the present invention includes methods of producing a nucleic acid molecule encoding an androgen responsive element III having a mutation that is associated with prostate cancer, wherein the mutation at position 4643, 5307, 5412 or 5429 in the promoter of the prostate specific antigen gene. Additionally, the present invention can include an oligonucleotide that hybridizing to the nucleic acid molecule.

The present invention also includes methods for detecting the presence of a genetic polymorphism associated with an androgen responsive element III in a sample of patient nucleic acid, comprising amplifying an androgen responsive promoter element gene sequence in the patient nucleic acid to produce an amplification product; and then identifying the presence of a genetic predisposition for increased cellular PSA production with the amplification product.

BRIEF DESCRIPTION OF DRAWINGS

FIG. 2A shows a comparison of the −4289 SNP. FIG. 2B shows a comparison of the −4330 polycytosine repeat. The right panel shows the PSA promoter haplotypes used to drive luciferase expression.

The polymorphism that differs between the two constructs is in bold and underlined. The arrows denote the direction from 5' to 3'. The gray box denotes the proximal PSA promoter and the approximate locations of the ARE I and ARE II sites. The left panel shows the results of the luciferase assay normalized to β-Gal (Relative Light Units). Each point represents the mean±standard error of 4 to 6 replicates. There are no significant differences between curves.

Figure 3:
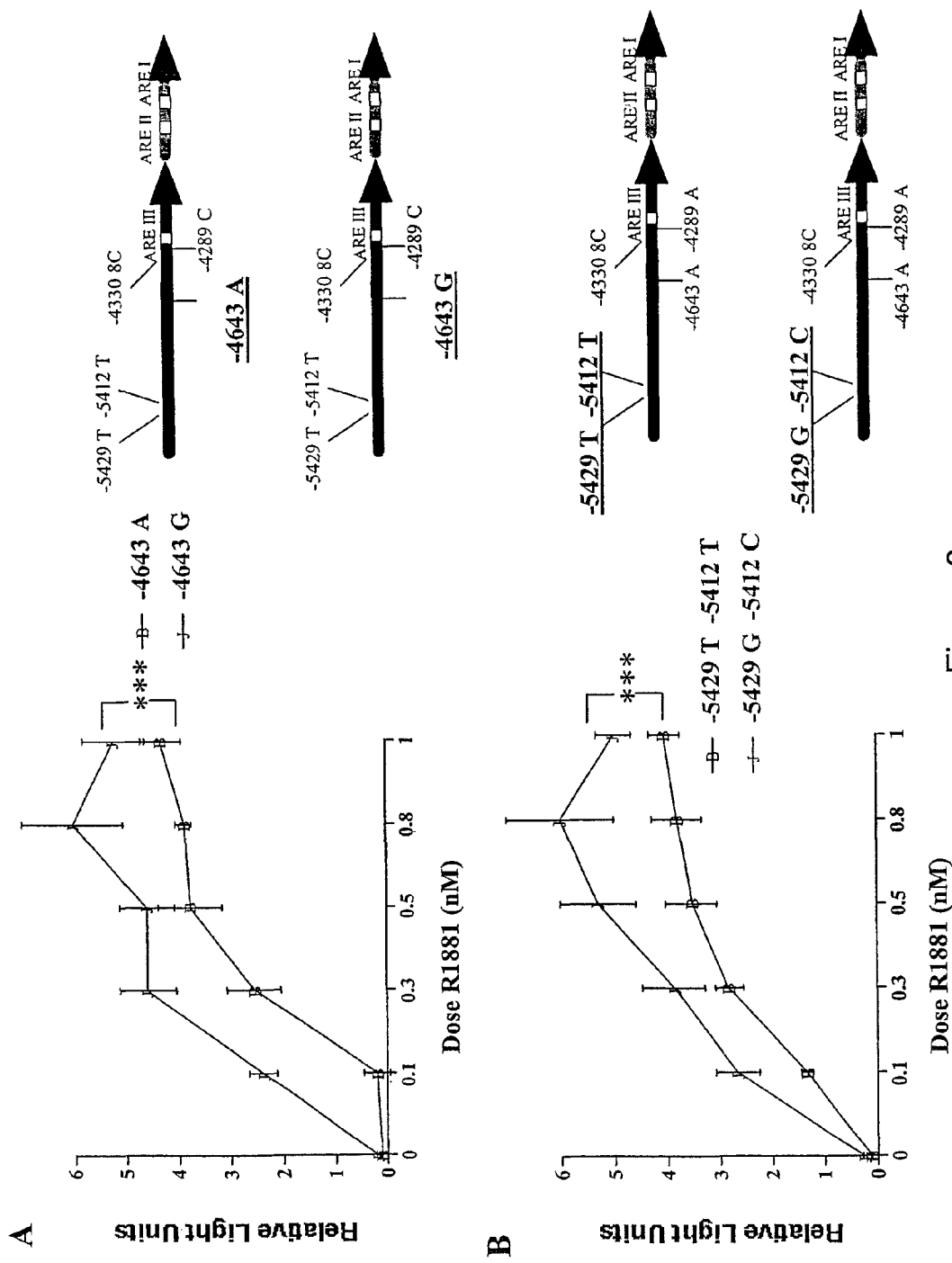

FIGS. 3A and 3B illustrate polymorphisms in the far upstream region of the PSA gene that affect promoter activity. FIG. 3A depicts a comparison between the two alleles of the −4643 SNP. FIG. 3B shows a comparison between the −5429/−5412 haplotypes. *** indicates the curves are significantly different by ANOVA at p≦0.001.

Figure 4:
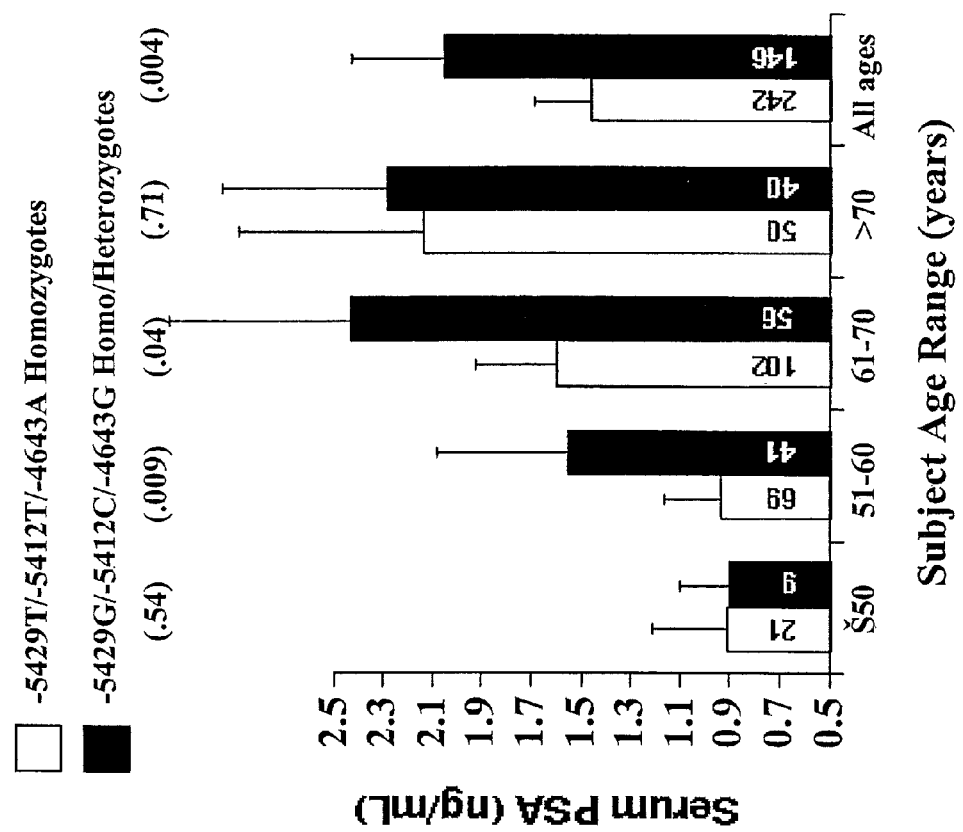

FIG. 4 illustrates PSA promoter haplotypes that are associated with age-adjusted serum PSA. The PSA promoter haplotypes were stratified by age and correlated with Log 10 transformed PSA as described in the Materials and Methods section. Each bar represents the mean±standard error. Numbers in bars indicate the number of subjects in each group used for analysis. Numbers in parentheses indicate the p-value.

DETAILED DESCRIPTION OF THE PREFERRED EMBODIMENTS

The present invention provides a method of screening (e.g., diagnosing or prognosing) for diseases, such as prostate cancer in a subject. The present invention relates to a method for the genetic diagnosis of prostate cancer as well as to probes for the genetic diagnosis of prostate cancer. The present invention also relates to methods of detecting increased PSA levels.

The term "Mutation" as used herein sometimes refers to a functional polymorphism that occurs in less than one percent of the population, and is strongly correlated to the presence of a gene (i.e., the presence of such mutation indicating a high risk of the subject being afflicted with a disease). However, "mutation" is also used herein to refer to a specific site and type of functional polymorphism, without reference to the degree of risk that particular mutation poses to an individual for a particular disease.

Subjects for screening and/or treatment with the present invention are, in general, human subjects, including male subjects. The subject may be of any race and any age, including juvenile, adolescent, and adult. It will be appreciated by those skilled in the art that, while the present methods are useful for screening subjects to provide an initial indication of the suitability of a patient for a particular treatment, this information will typically be considered by a clinician or medical practitioner in light of other factors and experience in reaching a final judgment as to the treatment which any given subject should receive.

Suitable subjects include those who have not previously been diagnosed as afflicted with prostate cancer, those who have previously been determined to be at risk of developing prostate cancer, and those who have been initially diagnosed as being afflicted with prostate cancer where confirming information is desired. Thus, it is contemplated that the methods described herein be used in conjunction with other clinical diagnostic information known or described in the art which are used in evaluation of subjects with prostate cancer or suspected to be at risk for developing such disease.

The detecting step may be carried out in accordance with known techniques, such as by collecting a biological sample containing DNA from the subject, and then determining the presence or absence of DNA encoding or indicative of the mutation in the biological sample. Any biological sample which contains the DNA of that subject may be employed, including tissue samples and blood samples, with blood cells being a particularly convenient source.

"Functional polymorphism" as used herein refers to a change in the base pair sequence of a gene that produces a qualitative or quantitative change in the activity of the protein encoded by that gene (e.g., a change in specificity of activity; a change in level of activity). The presence of a functional polymorphism indicates that the subject is at greater risk of developing a particular disease as compared to the general population. For example, the patient carrying the functional polymorphism may be particularly susceptible to chronic exposure to environmental toxins that contribute to prostate cancer. The term "functional polymorphism" includes mutations, deletions and insertions.

In general, the step of detecting the polymorphism of interest may be carried out by collecting a biological sample containing DNA from the subject, and then determining the presence or absence of DNA containing the polymorphism of interest in the biological sample. Any biological sample which contains the DNA of that subject may be employed, including tissue samples and blood samples, with blood cells being a particularly convenient source. The nucleotide sequence of the prostate specific antigen gene is known and suitable probes, restriction enzyme digestion techniques, or other means of detecting the polymorphism may be implemented based on this known sequence in accordance with standard techniques. See, e.g., U.S. Pat. Nos. 6,027,896 and 5,767,248 to A. Roses et al. (Applicants specifically intend that the disclosures of all United States patent references cited herein be incorporated by reference herein in their entirety).

Determining the presence or absence of DNA encoding a particular mutation may be carried out with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the particular mutation. Numerous different oligonucleotide probe assay formats are known which may be employed to carry out the present invention.

See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally, Kwoh et al., *Am. Biotechnol. Lab.* 8, 14-25 (1990). Examples of suitable amplification techniques include, but are not limited to, polymerase chain reaction, ligase chain reaction, strand displacement amplification (see generally G. Walker et al., *Proc. Natl. Acad. Sci. USA* 89, 392-396 (1992); G. Walker et al., *Nucleic Acids Res.* 20, 1691-1696 (1992)), transcription-based amplification (see D. Kwoh et al., *Proc. Natl. Acad Sci. USA* 86, 1173-1177 (1989)), self-sustained sequence replication (or "3SR") (see J. Guatelli et al., *Proc. Natl. Acad. Sci. USA* 87, 1874-1878 (1990)), the Qβ replicase system (see P. Lizardi et al., *BioTechnology* 6, 1197-1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA") (see R. Lewis, supra). Polymerase chain reaction is currently preferred.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. Such probes may be from 5 to 500 nucleotides in length, preferably 5 to 250, more preferably 5 to 100 or 5 to 50 nucleic acids. When PCR conditions allow for amplification of all allelic types, the types can be distinguished by hybridization with an allelic specific probe, by restriction endonuclease digestion, by electrophoresis on denaturing gradient gels, or other techniques.

Ligase chain reaction (LCR) is also carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

DNA amplification techniques such as the foregoing can, involve the use of a probe, a pair of probes, or two pairs of probes which specifically bind to DNA containing the functional polymorphism, but do not bind to DNA that does not contain the functional polymorphism. Alternatively, the probe or pair of probes could bind to DNA that both does and does not contain the functional polymorphism, but produce or amplify a product (e.g., an elongation product) in which a detectable difference may be ascertained (e.g., a shorter product, where the functional polymorphism is a deletion mutation). Such probes can be generated in accordance with standard techniques from the known sequences of DNA in or associated with a gene linked to prostate cancer or from sequences which can be generated from such genes in accordance with standard techniques.

It will be appreciated that the detecting steps described herein may be carried out directly or indirectly. Other means of indirectly determining allelic type include measuring polymorphic markers that are linked to the particular functional polymorphism, as has been demonstrated for the VNTR (variable number tandem repeats).

Kits for determining if a subject is or was (in the case of deceased subjects) afflicted with or is or was at increased risk of developing prostate cancer will include at least one reagent specific for detecting for the presence or absence of at least one functional polymorphism as described herein and instructions for observing that the subject is or was afflicted with or is or was at increased risk of developing prostate cancer if at least one of the functional polymorphisms is detected. The kit may optionally include one or more nucleic acid probes for the amplification and/or detection of the functional polymorphism by any of the techniques described above, with PCR being currently preferred.

Molecular biology comprises a wide variety of techniques for the analysis of nucleic acid and protein sequences. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, Molecular Cloning: A Laboratory Manual, 2 Ed., Cold spring Harbor Laboratory Press, Cold Spring Harbor, N.Y., 1989).

Most of these techniques involve carrying out numerous operations (e.g., pipetting, centrifugation, and electrophoresis) on a large number of samples. They are often complex and time consuming, and generally require a high degree of accuracy. Many a technique is limited in its application by a lack of sensitivity, specificity, or reproducibility.

For example, the complete process for carrying out a DNA hybridization analysis for a genetic or infectious disease is very involved. Broadly speaking, the complete process may be divided into a number of steps and sub-steps. In the case of genetic disease diagnosis, the first step involves obtaining the sample (e.g., saliva, blood or tissue). Depending on the type of sample, various pre-treatments would be carried out. The second step involves disrupting or lysing the cells which releases the crude DNA material along with other cellular constituents.

Generally, several sub-steps are necessary to remove cell debris and to further purify the DNA from the crude sample. At this point several options exist for further processing and analysis. One option involves denaturing the DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting the DNA to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out an amplification procedure such as the polymerase chain reaction (PCR) or the strand displacement amplification (SDA) method. These procedures amplify (increase) the number of target DNA sequences relative to non-target sequences Amplification of target DNA helps to overcome problems related to complexity and sensitivity in genomic DNA analysis. After these sample preparation and DNA processing steps, the actual hybridization reaction is performed. Finally, detection and data analysis convert the hybridization event into an analytical result.

Nucleic acid hybridization analysis generally involves the detection of a very small number of specific target nucleic acids (DNA or RNA) with an excess of probe DNA, among a relatively large amount of complex non-target nucleic acids. A reduction in the complexity of the nucleic acid in a sample is helpful to the detection of low copy numbers (i.e. 10,000 to 100,000) of nucleic acid targets. DNA complexity reduction is achieved to some degree by amplification of target nucleic acid sequences. (See, M. A. Innis et al., PCR Protocols: A Guide to Methods and Applications, Academic Press, 1990, Spargo et al., 1996, Molecular & Cellular Probes, in regard to SDA amplification). This is because amplification of target nucleic acids results in an enormous number of target nucleic acid sequences relative to non-target sequences thereby improving the subsequent target hybridization step.

The actual hybridization reaction represents one of the most important and central steps in the whole process. The hybridization step involves placing the prepared DNA sample in contact with a specific reporter probe at set optimal conditions for hybridization to occur between the target DNA sequence and probe.

Hybridization may be performed in any one of a number of formats. For example, multiple sample nucleic acid hybridization analysis has been conducted in a variety of filter and solid support formats (See Beltz et al., Methods in Enzymology, Vol. 100, Part et al., Eds., Academic Press, New York, Chapter 19, pp. 266-308, 1985). One format, the so-called "dot blot" hybridization, involves the non-covalent attachment of target DNAs to a filter followed by the subsequent hybridization to a radioisotope labeled probe(s). "Dot blot" hybridization gained wide-spread use over the past two decades during which time many versions were developed (see Anderson and Young, in Nucleic Acid Hybridization—A Practical Approach, Hames and Higgins, Eds., IRL Press, Washington, D.C. Chapter 4, pp. 73-111, 1985). For example, the dot blot method has been developed for multiple analyses of genomic mutations (EPA 0228075 to Nanibhushan et al.) and for the detection of overlapping clones and the construction of genomic maps (U.S. Pat. No. 5,219,726 to Evans).

Additional techniques for carrying out multiple sample nucleic acid hybridization analysis include micro-formatted multiplex or matrix devices (e.g., DNA chips) (see M. Barinaga, 253 Science, pp. 1489, 1991; W. Bains, 10 Bio/Technology, pp. 757-758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757-758, 1992). SBH makes use of all possible n-nucleotide oligomers (n-mers) to identify n-mers in an unknown DNA sample, which are subsequently aligned by algorithm analysis to produce the DNA sequence (See, Drmanac U.S. Pat. No. 5,202,231).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, (United Kingdom Patent Application GB 8810400, 1988; E. M. Southern et al., 13 Genomics 1008, 1992), proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency conditions for each oligonucleotide on an array.

Drmanac et al., (260 Science 1649-1652, 1993), used the second format to sequence several short (116 bp) DNA sequences. Target DNAs were attached to membrane supports ("dot blot" format). Each filter was sequentially hybridized with 272 labeled 10-mer and 11-mer oligonucleotides. Wide ranges of stringency conditions were used to achieve specific hybridization for each n-mer probe. Washing times varied from 5 minutes to overnight using temperatures from 0° C. to 16° C. Most probes required 3 hours of washing at 16° C. The filters had to be exposed from 2 to 18 hours in order to detect hybridization signals. The overall false positive hybridization rate was 5% in spite of the simple target sequences, the reduced set of oligomer probes, and the use of the most stringent conditions available.

Currently, a variety of methods are available for detection and analysis of the hybridization events. Depending on the reporter group (fluorophore, enzyme, radioisotope, etc.) used to label the DNA probe, detection and analysis are carried out fluorimetrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. Thus, detection of hybridization events is dependent upon how specific and sensitive hybridization can be made. Concerning genetic analysis, several methods have been developed that have attempted to increase specificity and sensitivity.

One form of genetic analysis is analysis centered on elucidation of single nucleic acid polymorphisms or ("SNPs"). Factors favoring the usage of SNPs are their high abundance in the human genome (especially compared to short tandem repeats, (STRs)), their frequent location within coding or regulatory regions of genes (which can affect protein structure or expression levels), and their stability when passed from one generation to the next (Landegren et al., *Genome Research*, Vol. 8, pp. 769-776, 1998).

A SNP is defined as any position in the genome that exists in two variants and the most common variant occurs less than 99% of the time. In order to use SNPs as widespread genetic markers, it is crucial to be able to genotype them easily, quickly, accurately, and cost-effectively. It is of great interest to type both large sets of SNPs in order to investigate complex disorders where many loci factor into one disease (Risch and Merikangas, Science, Vol. 273, pp. 1516-1517, 1996), as well as small subsets of SNPs previously demonstrated to be associated with known afflictions.

Numerous techniques are currently available for typing SNPs (for review, see Landegren et al., Genome Research, Vol. 8, pp. 769-776, (1998), all of which require target amplification. They include direct sequencing (Carothers et al., *BioTechniques*, Vol. 7, pp. 494-499, 1989), single-strand conformation polymorphism (Orita et al., *Proc. Natl. Acad. Sci. USA*, Vol. 86, pp. 2766-2770, 1989), allele-specific amplification (Newton et al., *Nucleic Acids Research*, Vol. 17, pp. 2503-2516, (1989), restriction digestion (Day and Humphries, *Analytical Biochemistry*, Vol. 222, pp. 389-395, 1994), and hybridization assays. In their most basic form, hybridization assays function by discriminating short oligonucleotide reporters against matched and mismatched targets. Many adaptations to the basic protocol have been developed. These include ligation chain reaction (Wu and Wallace, *Gene*, Vol. 76, pp. 245-254, 1989) and minisequencing (Syvanen et al., *Genomics*, Vol. 8, pp. 684-692, 1990). Other enhancements include the use of the 5'-nuclease activity of Taq DNA polymerase (Holland et al., *Proc. Natl. Acad. Sci. USA*, Vol. 88, pp. 7276-7280, 1991), molecular beacons (Tyagi and Kramer, *Nature Biotechnology*, Vol. 14, pp. 303-308, 1996), heat denaturation curves (Howell et al., *Nature Biotechnology*, Vol. 17, pp. 87-88, 1999) and DNA "chips" (Wang et al., *Science*, Vol. 280, pp. 1077-1082, 1998).

An additional phenomenon that can be used to distinguish SNPs is the nucleic acid interaction energies or base-stacking energies derived from the hybridization of multiple target specific probes to a single target. (See, R. Ornstein et al., "An Optimized Potential Function for the Calculation of Nucleic Acid Interaction Energies", *Biopolymers*, Vol. 17, 2341-2360 (1978); J. Norberg and L. Nilsson, *Biophysical Journal*, Vol. 74, pp. 394-402, (1998); and J. Pieters et al., *Nucleic Acids Research*, Vol. 17, no. 12, pp. 4551-4565 (1989)). This base-stacking phenomenon is used in a unique format in the current invention to provide highly sensitive Tm differentials allowing the direct detection of SNPs in a nucleic acid sample.

Additional methods have been used to distinguish nucleic acid sequences in related organisms or to sequence DNA. For example, U.S. Pat. No. 5,030,557 by Hogan et al. disclosed that the secondary and tertiary structure of a single stranded target nucleic acid may be affected by binding "helper" oligonucleotides in addition to "probe" oligonucleotides causing a higher Tm to be exhibited between the probe and target nucleic acid. That application however was limited in its approach to using hybridization energies only for altering the secondary and tertiary structure of self-annealing RNA strands which if left unaltered would tend to prevent the probe from hybridizing to the target.

With regard to DNA sequencing, K. Khrapko et al., Federation of European *Biochemical Societies Letters*, Vol. 256, no. 1, 2, pp. 118-122 (1989), for example, disclosed that continuous stacking hybridization resulted in duplex stabilization. Additionally, J. Kieleczawa et al., *Science*, Vol. 258, pp. 1787-1791 (1992), disclosed the use of contiguous strings of hexamers to prime DNA synthesis wherein the contiguous strings appeared to stabilize priming. Likewise, L. Kotler et al., *Proc. Natl. Acad. Sci. USA*, Vol. 90, pp. 4241-4245, (1993) disclosed sequence specificity in the priming of DNA sequencing reactions by use of hexamer and pentamer oligonucleotide modules. Further, S. Parinov et al., *Nucleic Acids Research*, Vol. 24, no. 15, pp. 2998-3004, (1996), disclosed the use of base-stacking oligomers for DNA sequencing in association with passive DNA sequencing microchips. Moreover, G. Yershov et al., *Proc. Natl. Acad. Sci. USA*, Vol. 93, pp. 4913-4918 (1996), disclosed the application of base-stacking energies in SBH on a passive microchip. In Yershov's example, 10-mer DNA probes were anchored to the surface of the microchip and hybridized to target sequences in conjunction with additional short probes, the combination of which appeared to stabilize binding of the probes. In that format, short segments of nucleic acid sequence could be elucidated for DNA sequencing. Yershov further noted that in their system the destabilizing effect of mismatches was increased using shorter probes (e.g., 5-mers). Use of such short probes in DNA sequencing provided the ability to discern the presence of mismatches along the sequence being probed rather than just a single mismatch at one specified location of the probe/target hybridization complex. Use of longer probes (e.g., 8-mer, 10-mer, and 13-mer oligos) were less functional for such purposes.

An additional example of methodologies that have used base-stacking in the analysis of nucleic acids includes U.S.

Pat. No. 5,770,365 by Lane et al., wherein is disclosed a method of capturing nucleic acid targets using a unimolecular capture probe having a single stranded loop and a double stranded region which acts in conjunction with a binding target to stabilize duplex formation by stacking energies.

Despite the knowledge of base-stacking phenomenon, applications as described above have not resulted in commercially acceptable methods or protocols for either DNA sequencing or the detection of SNPs for clinical purposes. We provide herein such a commercially useful method for making such distinctions in numerous genetic and medical applications by combining the use of base-stacking principles and electronically addressable microchip formats.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

The present invention also provides a method of conducting a clinical trial on a plurality of human subjects or patients. Such methods advantageously permit the refinement of the patient population so that advantages of particular treatment regimens (typically administration of pharmaceutically active organic compound active agents) can be more accurately detected, particularly with respect to particular subpopulations of patients. In general, such methods comprise administering a test active agent or therapy to a plurality of subjects (a control or placebo therapy typically being administered to a separate but similarly characterized plurality of subjects) and detecting the presence or absence of at least one mutation or polymorphism as described above in the plurality of subjects. The polymorphisms may be detected before, after, or concurrently with the step of administering the test therapy. The influence of one or more detected polymorphisms or absent polymorphisms on the test therapy can then be determined on any suitable parameter or potential treatment outcome or consequence, including but not limited to: the efficacy of the therapy, lack of side effects of the therapy, etc.

In describing the mutations disclosed herein in the novel proteins described herein, and the nucleotides encoding the same, the naming method is as follows: [nucleic acid replaced] [nucleic acid number in sequence of known sequence][alternate nucleic acid]. For example, for the $4643^{rd}$ position is guanine and is replaced with an adenine.

Embodiments of the present invention further characterize the PSA gene for polymorphisms and determine the associations of these polymorphisms with serum PSA. Previous work by Xue et al. suggested a role for the PSA −158 SNP in modulating serum PSA in men without prostatic disease. In that study, the −158 AA genotype was associated with higher serum PSA levels relative to the PSA levels in subjects with the −158 AG or GG genotypes. However, others were not able to reproduce these results, and functional studies found no role for the −158 SNP in regulating PSA promoter activity.

Embodiments of the present invention illustrate that the linkage disequilibrium and haplotype analyses demonstrate that the −158 A allele is exclusively linked to the far upstream haplotype that is associated with lower serum PSA and has lower functional activity in vitro. The −158 G allele can be distributed between both the weak and strong far upstream haplotypes. This difference in distribution between the −158 G and A alleles with weak and strong haplotypes in the far upstream region of the PSA gene can result in the association of the −158 SNP with serum PSA observed by Xue et al.

Embodiments of the present invention include 3 SNPs that were associated with serum PSA. An A/G SNP at −4643 had a 19.6% prevalence (G allele), and was associated with a 15-30% increase in serum PSA (p=0.017), and luciferase reporter assays demonstrated a 20-30% increase in promoter activity. A T/C SNP at −5412 had a 21.6% prevalence (C allele), and was very strongly associated with a 20-40% increase in serum PSA (p=0.0015). The third SNP at −5429 (T/G) was in strong linkage disequilibrium with the −5412 SNP. The G allele had a 21.4% prevalence and was strongly associated with a 30-40% increase in serum PSA (p=0.021). Luciferase reporter assays demonstrated that the −5412 C/−5429 G haplotype had 20-30% greater promoter activity relative to the −5412 T/−5429 T haplotype. Additionally, men with AG or GG genotypes at the SNP −5307A/G have statistically significantly higher PSA levels than men with an AA genotype.

As noted above, the present invention includes methods of identifying a subject at risk for a genetic predisposition for increased cellular PSA production, comprising detecting the presence or absence of a mutation at position 4643, 5307, 5412 and 5429 of the prostate specific antigen gene promoter in the subject; and determining that the subject is at an increased risk of a genetic predisposition for increased cellular PSA production due to the presence or absence of the mutation in the prostate specific antigen gene promoter. The test for a genetic predisposition for increased cellular PSA production may also identify subjects at risk for prostate cancer. Thus, both healthy and affected subjected may be tested.

The present invention also includes methods of diagnosing prostate cancer or a genetic predisposition for developing prostate cancer in a human subject by providing a biological sample from the subject wherein the sample encodes a promoter of the prostate specific antigen, detecting one or more mutations in the biological sample, and determining that the subject has at least one detected mutation in each genomic copy of the biological sample encoding the promoter of the prostate specific antigen, wherein the presence of at least one detected mutation in each copy of the sequence encoding the promoter of the prostate specific antigen is diagnostic for prostate cancer or a genetic predisposition for developing prostate cancer in the subject, and wherein the mutation occurs at position 4643, 5307, 5412 or 5429 in the promoter of the prostate specific antigen gene. The lack of mutations in the prostate specific antigen can indicate that a subject is at a reduced risk of developing prostate cancer.

The present invention also includes methods of identifying a subject with increased prostate serum level comprising detecting the presence or absence of a mutation at position 4643, 5307, 5412 and 5429. The overall survival rate of prostate cancer patients with elevated serum levels is significantly lower than those with normal or decreased serum levels. Therefore, increased prostate serum levels can indicate a risk of development of prostate cancer. Thus, the present invention can include a test for increased serum levels to determine if a subject is at an increased or reduced risk of prostate cancer.

The present invention also includes methods for detecting the presence of a genetic polymorphism associated with an androgen responsive element III in a sample of patient nucleic acid, comprising amplifying an androgen responsive promoter element gene sequence in the patient nucleic acid to produce an amplification product; and then identifying the presence of a genetic predisposition for increased cellular PSA production with the amplification product. These methods allow for the identification of additional mutants in an androgen responsive promoter element.

The present invention is explained in greater detail in the following non-limiting examples.

EXAMPLES

Figure 1:
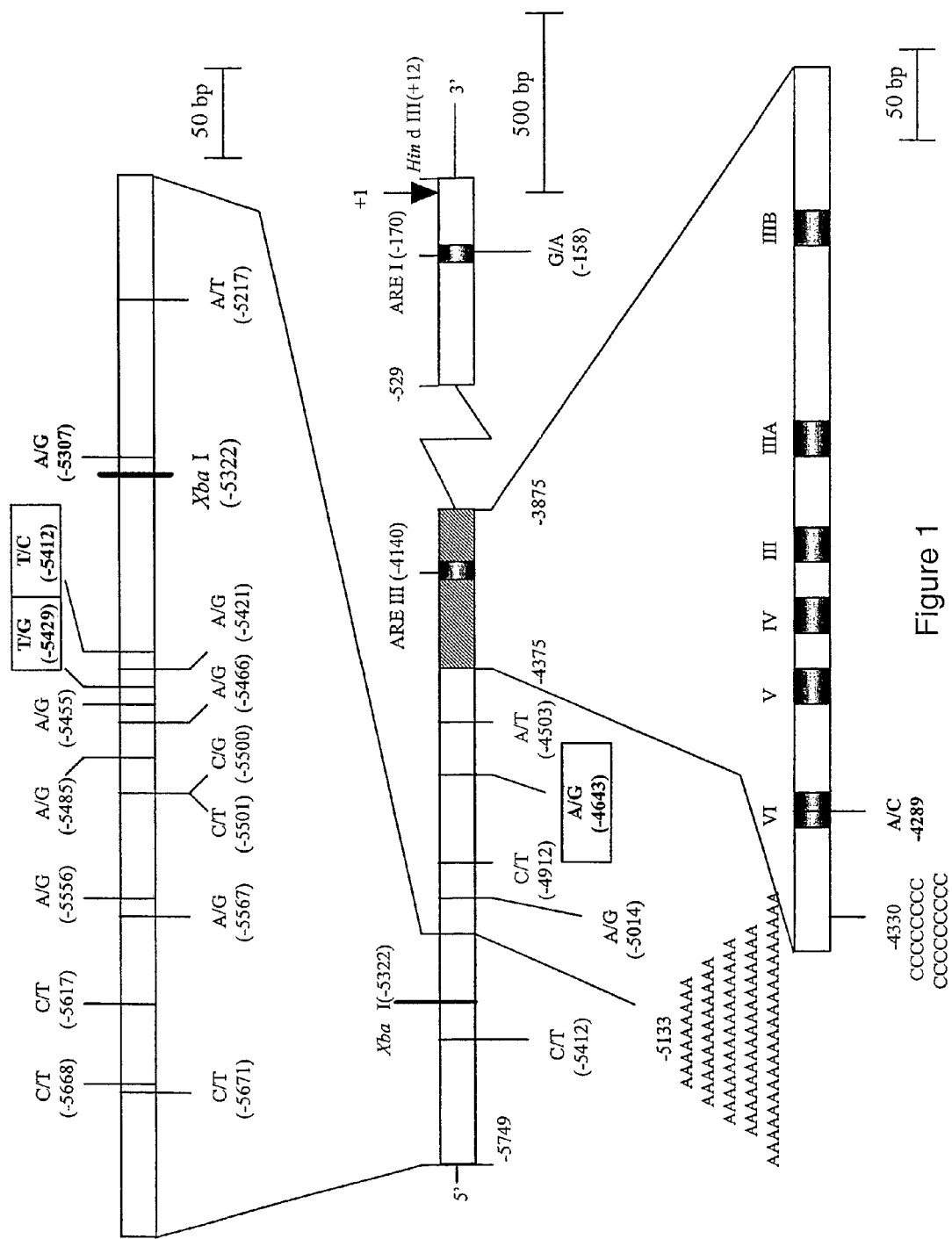
FIG. 1 illustrates the schematic structure and variance in the PSA promoter between −3875 to −5749. The base changes are depicted with the most common variant first. Numbers under the nucleotide variants are the location (or center when it is a polynucleotide repeat) relative to the sequence originally published. The putative AREs are depicted by shaded boxes. The relative scale in basepairs (bp) of each bar is indicated to the lower right of each bar. Polymorphisms that are significantly associated (p<0.05) with age-adjusted serum PSA are depicted in bold. Those that are also boxed are strongly associated (p<0.01) with age-adjusted serum PSA and affect the functional activity of the PSA promoter constructs.
Figure 2:
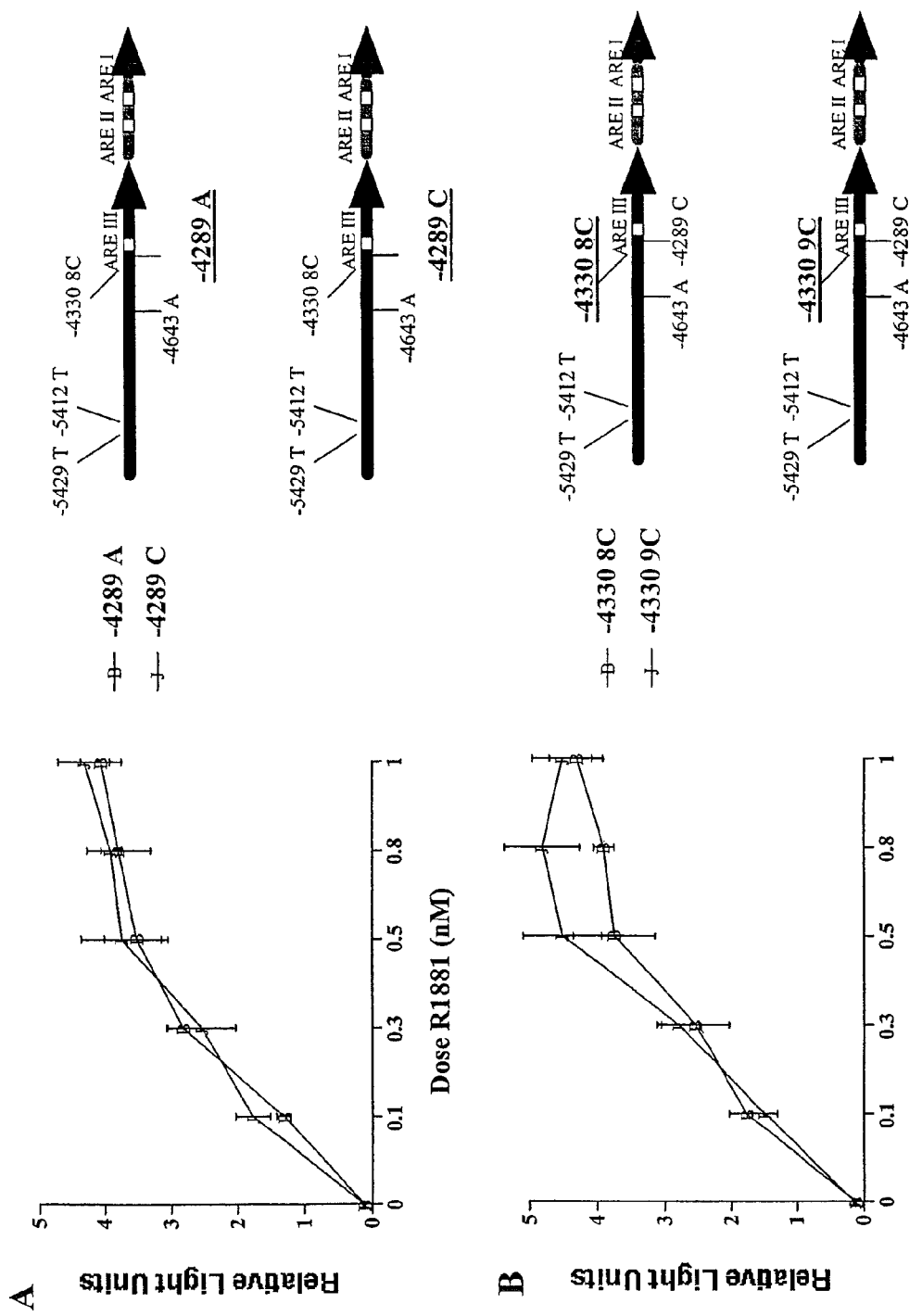
FIGS. 2A and 2B depict polymorphisms in the ARE III androgen responsive region that do not affect PSA promoter activity. These figures illustrate LNCaP cells that were transiently transfected with luciferase reporter constructs and pCMV β-Gal and treated with increasing concentrations of R1881 for 24 hrs. At the end of the incubation cells were harvested and luciferase and β-Gal activities were determined as described in the Materials and Methods section. Comparison of differences between groups was performed by ANOVA, p≦0.05 was considered significant.

Association of Sequence Variants in the ARE III Region with Serum PSA Levels The androgen responsive ARE III region is located between −3800 to −4300 in the PSA gene. Direct sequencing of this region of PCR products from previously reported group of subjects identified 2 polymorphisms in this region (FIG. 1). Neither of these polymorphisms is reported in the NCBI SNP database. SNP −4289A/C is located in the low affinity, non-consensus ARE termed ARE VI. The allele C of this SNP, with an estimated frequency of 0.20, was associated with elevated PSA levels. Men with AC or CC genotypes at this SNP have significantly higher PSA levels than men with AA genotype (P=0.017, age adjusted, Table 1). Excluding men with PSA of 9.0 ng/ml or higher did not significantly affect this result (P=0.028, Table 1) The other polymorphism in this region is a poly-cytosine tract that varied between 8 and 9 nucleotides in length and was centered at −4330 in the PSA promoter (FIG. 1). This polymorphism was not in Hardy-Weinberg equilibrium in our study subjects. Therefore, no association tests were performed for this variant.

TABLE 1

Frequencies of SNPs in PSA promoter region among white study subjects (N = 409)*

| Location of SNP† | Nucleotide change | Percentage of chromosome carrying SNP in Caucasians (N)‡ |
|---|---|---|
| −5567:AY283612 | G to A | 9.16 (74/808) |
| −5501:AY283614 | T to C | 2.23 (17/762) |
| −5466:AY283615 | G to A | 1.97 (15/761) |
| −5429:rs2569733 | T to G | 23.0 (186/808) |
| −5412:rs2739448 | T to C | 22.0 (176/802) |
| −5307:rs266868 | G to A | 39.8 (240/806) |
| −5217:rs266867 | T to A | 9.23 (74/802) |
| −4643:rs925013 | A to G | 21.2 (171/806) |
| −4289:AY283613 | A to C | 20.9 (171/818) |

Association of SNPs in the Far Upstream Region of the PSA Promoter with Serum PSA Levels The present study includes a sequencing of the remaining 1.2 kb of the 5' region of PCR amplified DNA from 20 subjects. This analysis identified an additional 6 relatively common SNPs, a poly-adenosine tract that varied between 9 and 22 A's, and several less frequent variants (Table 2, FIG. 1). Five of the common SNPs are present in the NCBI SNP database (Table 1), the remainder are previously unreported SNPs. The entire spectrum of variants is depicted in FIG. 1. The frequencies of SNPs are listed in Table 2. Only the 6 relatively common SNPs were evaluated for association with serum PSA. Two SNPs (−5217A/T and −5567A/G) had no statistically significant association with serum PSA. Men with AG or GG genotypes at the SNP −5307A/G have statistically significantly higher PSA levels than men with AA genotype (P=0.017, age adjusted, Table 1).

TABLE 2

Serum PSA levels and sequence variants in PSA gene promoter region among the white study subjects *

| SNP/Genotype † | N | log10 (PSA) Mean | log10 (PSA) SD | PSA geometric mean | P ‡ | P § | P ‖ |
|---|---|---|---|---|---|---|---|
| −158:rs266882 (ARE I)** | | | | | | | |
| GG | 109 | −0.026 | 0.40 | 0.94 | | | |
| GA | 215 | 0.079 | 0.40 | 1.20 | | | |
| AA | 96 | 0.008 | 0.39 | 1.02 | .061 | .06 | .12 |
| −4289:AY283613 (ARE VI) | | | | | | | |
| AA | 256 | −0.006 | 0.39 | 0.99 | | | |
| AC | 135 | 0.112 | 0.41 | 1.29 | | | |
| CC | 18 | 0.062 | 0.48 | 1.15 | .021 | .017 | .028 |
| −4643:rs925013 (Nco I) | | | | | | | |
| AA | 250 | 0.0004 | 0.39 | 1.00 | | | |
| AG | 135 | 0.122 | 0.39 | 1.32 | | | |
| GG | 18 | 0.062 | 0.48 | 1.15 | .017 | .0095 | .015 |
| −5217:rs266867 | | | | | | | |
| TT | 331 | 0.049 | 0.40 | 1.12 | | | |
| TA | 66 | 0.049 | 0.42 | 1.12 | | | |
| AA | 4 | −0.33 | 0.46 | 0.47 | .18 | .46 | .86 |
| −5307:rs266868 | | | | | | | |
| GG | 198 | 0.09 | 0.42 | 1.23 | | | |
| GA | 170 | 0.004 | 0.38 | 1.01 | | | |
| AA | 35 | −0.017 | 0.39 | 0.96 | .074 | .017 | .035 |
| −5412:rs2739448 (BstUI) | | | | | | | |
| TT | 246 | −0.012 | 0.38 | 0.97 | | | |
| TC | 134 | 0.141 | 0.41 | 1.38 | | | |
| CC | 21 | 0.076 | 0.49 | 1.19 | .0015 | <.001 | .0045 |

TABLE 2-continued

Serum PSA levels and sequence variants in PSA gene promoter region among the white study subjects *

| SNP/Genotype † | N | log10 (PSA) Mean | SD | PSA geometric mean | P ‡ | P § | P ‖ |
|---|---|---|---|---|---|---|---|
| −5429:rs2569733 (Fok I) | | | | | | | |
| TT | 245 | 0.005 | 0.40 | 1.01 | | | |
| TG | 132 | 0.118 | 0.39 | 1.31 | | | |
| GG | 27 | 0.086 | 0.44 | 1.22 | .021 | .009 | .012 |
| −5567:AY283612 | | | | | | | |
| GG | 334 | 0.057 | 0.41 | 1.14 | | | |
| GA | 66 | −0.015 | 0.34 | 0.97 | | | |
| AA | 4 | 0.03 | 0.41 | 1.07 | .41 | .44 | .8 |

The remaining 3 SNPs (−4643A/G, 5412T/C, and −5429T/G) were strongly associated with serum PSA levels (Table 1). The G allele of the SNP −4643A/G, with an estimated frequency of 0.21, was associated with increased PSA levels. Men with GA or GG genotypes at this SNP have significantly higher PSA levels than men with AA genotype (P=0.0095, age adjusted). Luciferase reporter assays demonstrated that the G allele at −4643 was more potent as a promoter than the A allele at −4643, at all androgen levels tested (FIG. 3A). This difference in promoter activity was between 18 and 40% depending on the androgen concentration (P<0.001).

The C allele of the SNP −5412T/C, with an estimated frequency of 0.22, was associated with elevated PSA levels. Men with TC or CC genotypes at this SNP have significantly higher PSA levels than men with TT genotype (P=0.0009, age adjusted). Similarly, the G allele of the SNP −5429T/G, with an estimated frequency of 0.21, was also associated with higher PSA levels. Men with TG or GG genotypes at this SNP have significantly higher PSA levels than men with TT genotype (P=0.009, age adjusted). Excluding samples with PSA of 9.0 or greater did not significantly affect the association results for either of these SNPs. FIG. 3B demonstrates that the G-C haplotype conferred significantly greater promoter activity than the T-T haplotype (P=0.001).

Comprehensive Assessment of Associations of Multiple PSA Gene Promoter Polymorphisms with Serum PSA Levels The three promoter SNPs (−4643A/G, −5412T/C, and −5429T/G) were tested for whether a combination of these sequence variants impose a stronger association with serum PSA levels. As shown below in Table 3, there existed only two major haplotypes in the study population, either a haplotype with all three alleles associated with higher PSA levels and promoter activities (−5429G/−5412C/−4643G), with an estimated frequency of 0.20, or a haplotype with all three alleles associated with lower PSA levels and promoter activities (−5429T/−5412T/−4643A), with an estimated frequency of 0.77. The effect of the haplotypes on the association of PSA levels was estimated. The results are depicted in FIG. 4. Men with at least one copy of the G-C-G haplotype had 35% higher PSA levels than men with homozygous T-T-A haplotype (P=0.004, adjusted for age). This trend was observed in each of the four age decades (FIG. 4).

TABLE 3

Association of PSA promoter haplotypes and serum PSA levels*

| Haplotype | −5429 | −5412 | −4643 | Frequency | Score test† | (P)‡ |
|---|---|---|---|---|---|---|
| 1 | T | T | A | 0.77 | −3.33 | (<.001) |
| 2 | G | C | G | 0.2 | 2.51 | (.009) |
| 3 | G | C | A | 0.01 | 0.43 | (.65) |
| Global | | | | | 13.84 | (.003) |

*PSA = prostate-specific antigen.
†HAPLOSCORE program statistic
‡The P-value of a $\chi^2$ test of score statistic. Adjusted for age.

Pairwise linkage disequilibrium demonstrated that nearly all of the major PSA promoter SNPs are in strong linkage disequilibrium (Table 4). This includes the −158 SNP with farther upstream SNPs. The exception to this is the T/A −5217 SNP with G/A −5567 and A/C −4289. We next determined the major haplotypes of the 3 SNPs that had significant association with serum PSA and the −158 SNP. The data demonstrated that between these 4 SNPs there are 3 haplotypes that account for 97% of the PSA gene sequences evaluated in the study population. The A −158 SNP is exclusively linked with a single haplotype that has T, T, A at positions −5429, −5412, −4643, respectively. 62% of the G −158 SNP is linked with this same T −5429, T −5412, A −4643 haplotype in the far upstream enhancer. The remaining 38% is linked with the G −5429, C −5412, G −4643 haplotype.

TABLE 4

Pair-wise test of linkage disequilibrium of SNPs in the PSA gene promoter*

| | (−5567) | (−5429) | (−5412) | (−5307) | (−5217) | (−4643) | (−4289) | (−158) |
|---|---|---|---|---|---|---|---|---|
| (−5567) | | 1.000 | 1.000 | 0.975 | 0.433 | 1.000 | 1.000 | 1.000 |
| (−5429) | .016 | | 0.968 | 1.000 | 1.000 | 0.958 | 0.963 | 0.834 |
| (−5412) | .010 | .000 | | 1.000 | 1.000 | 0.938 | 0.941 | 0.847 |
| (−5307) | .000 | .000 | .000 | | 1.000 | 1.000 | 1.000 | 0.426 |
| (−5217) | 1.000 | .010 | .004 | .012 | | 1.000 | 1.000 | 1.000 |
| (−4643) | .007 | .000 | .000 | .000 | .040 | | 1.000 | 1.000 |

TABLE 4-continued

Pair-wise test of linkage disequilibrium
of SNPs in the PSA gene promoter*

|          | (−5567) | (−5429) | (−5412) | (−5307) | (−5217) | (−4643) | (−4289) | (−158) |
|----------|---------|---------|---------|---------|---------|---------|---------|--------|
| (−4289)  | .018    | .000    | .000    | .000    | .096    | .000    |         | 0.960  |
| (−158)   | .000    | .000    | .000    | .000    | .000    | .000    | .000    |        |

*Upper right cells above the blank diagonal show the absolute value of Lewontin's D', an estimate the strength of pairwise linkage disequilibrium, and lower left cells below the blank diagonal show the associated P values.
SNPs = single nulcleotide polumorphisms;
PSA = prostate-specific antigen.

Materials and Methods

Subjects

The subjects consisted of 518 male painters, plumbers, pipefitters, heavy equipment operators, and electricians in which PSA levels were assessed to determine the risk of prostate cancer after asbestos exposure. All subjects gave informed consent, received a physical examination, and complete medical and occupational history were obtained. Whole blood collected at the time of examination was used for DNA isolation and determination of serum PSA levels. 49 subjects were African-American and were excluded from the present study. 27 patients were excluded from the present study due to the presence of prostate cancer. 14 patients were excluded because of undetectable PSA ($\leq 0.1$ ng/ml). 19 DNA samples failed to yield a PCR product in the target region or there was insufficient DNA for amplification. The analyses were conducted on the remaining 409 samples. The mean age was 63.7 and the median PSA was 1.01 ng/ml (range: 0.14-20.7 ng/ml). 71 subjects have PSA $\geq 2.5$ ng/ml, 36 subjects have PSA $\geq 4$ ng/ml, and 11 subjects have PSA $\geq 9$ ng/ml.

PCR Amplifications

Nested PCR was used to amplify a 1.9 kb region of the PSA gene encompassing nucleotides −3875 to −5749 relative to the transcription start site using the numbering of the PSA gene reported by Schuur et al. Between 25-70 ng of genomic DNA derived from peripheral lymphocytes was used as a template in a 100 µl PCR reaction volume. In the first set of reactions, each tube contained 1× Thermophilic DNA Polymerase buffer (Promega, Madison, Wis.), 2.5 mM $MgCl_2$, 100 µM of each dNTP (Promega, Madison, Wis.), 150 nM of each primer, 5 U Taq DNA Polymerase (Promega, Madison, Wis.) and 0.2 U Vent DNA polymerase (New England Biolabs, Beverley, Mass.). The sequence of the 5' primer was: 5'TTTGGCAGTGGAGTGCTGC 3' (SEQ ID NO: 1). The sequence of the 3' primer was: 5'GCTTTGGAATATCCCTGCCAG 3' (SEQ ID NO: 2). In the nested set of PCR reactions 10 µl of the first reaction was used as template with internal 5' primer 5'ATGAATTCGTCGACCACAGTGTAATGCCATCCAGG 3' (SEQ ID NO: 3) and 3' primer 5'ATAGGATCCAGACTGTCCTGCAGACAAGG 3' (SEQ ID NO: 4) which introduced unique Sal I or Bam HI restriction sites, respectively (underlined). In the first set of reactions, the samples were heated to 94° C. for 5 min, then 80° C. for 10 min. After 1 min at 80° C. DNA polymerase was added. Subsequent to this, 30 amplification reactions were carried out as follows: 95° C., 1 min; 50° C., 1 min; 72° C., 1 min. A final extension was performed at 72° C. for 7 minutes. All reaction conditions were identical in the nested amplification except that after the 10 min incubation at 80° C. an initial 3 cycles of 94° C., 1 min; 50° C., 1 min; 72° C., 1 min were performed followed by 27 cycles of 94° C., 1 min; 58° C., 1 min; and 72° C., 1 min. Samples were stored at 4° C. until they were used. This PCR reaction was used directly for genotyping by sequencing or RFLP analysis and for subcloning for luciferase reporter constructs as described below.

Genotyping by DNA Sequencing

Sequence variants were identified by DNA sequencing PCR products (generated as described above) from 20 random DNA samples from our study subjects. DNA sequencing was performed using the ABI BigDye Terminator sequencing kit (Applied Biosystems, Inc., Foster City, Calif.). Each plate contained DNA subjects with various phenotypes (subjects with higher or lower PSA levels), as well as two known samples sequenced in duplicate and two blanks. Each 10 µl sequencing reaction contained 10-50 ng of purified PCR product, 1.5 pmoles of sequencing primer, 1 µl of BigDye Terminator mix, 1.5 µl of 5× sequencing dilution buffer (400 mM Tris pH 9.0, 10 mM $MgCl_2$) and water to volume. Cycling conditions were 94° for 1 min; 25 cycles of 94° C. for 30 sec, 50° C. for 30 sec, and 60° C. for 4 min; and finishing with a single 72° C. extension step for 5 min. Sequencing products were ethanol precipitated, air-dried, resuspended in 25 µl $ddH_2O$, and analyzed on an ABI 3700 DNA Analyzer. DNA sequencing data were aligned and polymorphisms identified using Sequencher DNA analysis software (Gene Codes Corporation, Ann Arbor, Mich.). Primers used for sequencing were 5' CCTTCAGGTGAACAAAGG 3' (SEQ ID NO: 5), 5' AGACCAGGGACACTCTGG 3' (SEQ ID NO: 6), 5' TCACATTAGTACACCTTGCCC 3 (SEQ ID NO: 7)', 5' TAGACTGCTCTGGTCACCC 3' (SEQ ID NO: 8), 5' GGACAGGGACATCAGGCC 3' (SEQ ID NO: 9), 5' GCTTTGGAATATCCTGCCAG 3' (SEQ ID NO: 10). The 5' and 3' ends were sequenced with the internal PCR primers for direct sequencing of PCR products, or T3 and T7 primers for sequencing pBluescript clones.

Nco I Restriction Fragment Length Polymorphism Analysis

Ten µl of the PCR products were digested to completion (greater than 3 hrs) with Nco I (Promega, Madison, Wis.) restriction enzyme according to the manufacturer's recommended conditions. Digested products were fractionated on 1% agarose gels and visualized by ethidium bromide staining. Intact PCR product was run in a parallel lane as a control. The presence of a recognition site for the variable Nco I site (G at nucleotide −4643) results in the formation of three bands of 1100, 700 and 100 bp.

Luciferase Reporter Constructs

DNA samples from individuals homozygous for specific SNPs were identified by sequencing as described above and were used as template to clone specific desired haplotypes. Lymphocyte DNA PCR reaction products were digested sequentially with Sal I and Bam HI (Promega, Madison, Wis.) and cloned into the Sal I and Bam HI sites of pBluescript SKIT (Promega, Madison, Wis.). Plasmid DNA was isolated from positive clones for nucleic acid sequence analysis as described above. The nucleotide sequence from the cloned product was compared to the deduced sequence from the PCR product. Only clones that were identical to the genomic sequence were used for subsequent steps. After sequence verification the positive clones were digested with Kpn I and Sac I (Promega, Madison, Wis.), whose sites flank the 1.9 kb insert. The inserts were subcloned into the luciferase reporter vector pGL3Basic (Promega, Madison, Wis.) at the Kpn I and Sac I sites of the vector. The pGL3Basic vector used to make the constructs had at the Hind III site a 525 base pair fragment of the proximal PSA promoter, including ARE I (−158 G allele), ARE II and the transcription start site driving reporter gene expression. All final reporter constructs were validated by nucleotide sequencing.

Luciferase Assays

All experiments were conducted using the prostate cancer cell line LNCaP (American Type Culture Collection, Rockville, Md.). Briefly, the cells were plated at $1.5 \times 10^5$ cells/well in 6-well tissue culture plates in RPMI 1640 supplemented with 10% fetal bovine serum. Forty-eight hr later the medium was removed from each well and 1 ml of Lipofectamine (Invitrogen Life Technologies, Carlsbad, Calif.) and plasmid cocktail were added to each well. This amount of cocktail contains 1.25 μg of luciferase reporter plasmid DNA, 0.25 μg of pCMV-β-gal plasmid DNA (to control transfection efficiency), and 8 μl of Lipofectamine reagent. After 5 hr of incubation the transfection cocktail was removed, and fresh medium (RPMI-1640 supplemented with 10% charcoal stripped fetal bovine serum) was added to the cells. Twenty-four hr after transfection the cells were switched to experimental media containing the indicated doses of synthetic androgen R1881 (NEN Life Science Products, Inc. Boston, Mass.), and allowed to incubate an additional 24 hr. At the end of the 24 hr incubation cell lysates were made using the cell lysis buffer provided in the Promega luciferase assay kit (Promega, Madison, Wis.) and luciferase activity was measured in a Turner 2D luminometer using 20 μl of lysate and the protocol provided with the Promega luciferase assay kit (Promega, Madison, Wis.).

To control for transfection efficiency n-gal expression plasmid was included in the transfection cocktail (see above). A 5 μl aliquot of each transfection lysate was used to measure β-gal expression by incubating for 1.5 hrs at 37° C., with 100 μl of o-nitrophenyl-b-D-galactopyranoside buffer (200 mM sodium phosphate buffer, pH 7.3, 2 mM $MgCl_2$, 100 mM β-Mercaptoethanol, 1.33 mg/ml o-nitrophenyl-b-D-galactopyranoside). The reaction was terminated with 100 μl of 1M sodium carbonate and absorbance at 405 nm was determined on a Molecular Devices microtiter plate reader (Molecular Devices, Palo Alto, Calif.). A standard curve was constructed using varying amounts of a cell extract from LNCaP cells transfected with pCMV-β-gal. Each standard and unknown was assayed in duplicate. The unknown values were interpolated from the linear range of the standard curve using the SoftMax program provided by the manufacturer of the microtiter plate reader. One β-gal unit is defined as 2 μl of standard cell extract. Each experimental condition was performed in 6 replicate wells (2 wells on each of 3 separate culture plates). The experiments were repeated twice. Results of a representative experiment are expressed as the mean±standard error (luminometer units per unit of β-gal expression).

Statistical Methods

Hardy-Weinberg equilibrium tests for all genotyped SNPs, and pair-wise linkage disequilibrium tests for all pairs of genotyped SNPs, were performed among Caucasian subjects using the GDA computer program and SAS/Genetics (2002). Weir B. Genetic data analysis II: Methods for discrete population genetic data. Boston, Mass.: Sinauer Association, Inc.; 1996. The Hardy-Weinberg equilibrium tests are based on exact tests, where a large number of the possible arrays are generated by permuting the alleles among genotypes, and the proportion of these permuted genotypic arrays that have a smaller conditional probability than the original data is calculated. Tests for pair-wise linkage disequilibrium are based on an exact test assuming multinomial probability of the multilocus genotype, conditional on the single-locus genotype. A Monte Carlo simulation was used to assess the significance, by permuting the single-locus genotypes among individuals in the sample to simulate the null distribution. The empirical p-values of both the Hardy-Weinberg equilibrium and linkage disequilibrium tests were based on 10,000 replicate samples. The Lewontin's D' was used to estimate strength of pair-wise linkage disequilibrium. Devlin B, Risch N. A comparison of linkage disequilibrium measures for fine-scale mapping. Genomics 1995; 29:311-22.

PSA levels were log 10 transformed because the distribution of serum PSA levels deviated significantly from a normal distribution (Kolomogorov D statistics=0.24; P<0.01). After log transformation, the distribution approached normality but remained significantly different from a normal distribution (D=0.09; P<0.01). ANOVA tests were performed to test for differences in mean log PSA levels among men with different genotypes for each SNP. Multiple regression models were used to estimate the effects of the genotypes, with either dominant or recessive models, adjusted for the variation of age. To decrease the potential population stratification, all analyses were limited to Caucasians.

Haplotype frequency was estimated using the statistical method proposed by Stephens et al., as implemented in the computer program PHASE. Stephens M, Smith N J, Donnelly P. A new statistical method for haplotype reconstruction from population data. Am J Hum Genet 2001; 68:978-89. Association between the haplotypes and serum PSA was performed using a score test developed by Schaid et al., as implemented in the computer program HAPLO.SCORE for the S-PLUS programming language or for the R programming language). Schaid et al., Score tests for association between traits and haplotypes when linkage phase is ambiguous. Am J Hum Genet 2002; 70:425-34. Age variation was modeled in the haplotype score test.

Comparisons of transfection data were conducted using a two-way ANOVA controlling for R1881 dose and haplotype of the expression construct, with post-hoc analysis by Tukey-Kramer test. $P \leqq 0.05$ was considered significant.

The foregoing is illustrative of the present invention, and is not to be construed as limiting thereof. The invention is defined by the following claims, with equivalents of the claims to be included therein.

What is claimed is:

1. A method of screening a human male subject for a genetic predisposition for increased serum PSA levels, comprising:
    detecting the presence or absence of an A/G mutation wherein said mutation is at position −5307 in the promoter of the prostate specific antigen (PSA) gene in a biological sample collected from said subject, said sample comprising DNA containing said promoter of the PSA gene; and
    determining that the subject is at an increased risk of a genetic predisposition for increased serum PSA levels if a G is present at nucleotide position −5307 of the promoter of the PSA gene.

2. The method of claim 1, wherein the detecting step includes a probe hybridization step.

3. The method of claim 1, wherein the detecting step includes a nucleic acid amplification step.

4. The method of claim 1, wherein the detecting step includes a polymerase chain reaction step.

5. The method of claim 1, wherein said detecting step further comprises detecting whether said subject is homozygous for said mutation.

6. A method for identifying a human male subject having an increased risk for having increased serum prostate specific antigen (PSA) levels, comprising:
    obtaining a sample comprising DNA from the subject, wherein said DNA contains a promoter of the PSA gene,
    determining the nucleotide present at nucleotide position −5307 of said promoter of the PSA gene, and
    determining that said subject has increased risk for having increased serum PSA levels if a G is present at nucleotide position −5307 of the promoter sequence of the PSA gene.

7. The method of claim 6, wherein the detecting step includes a probe hybridization step.

8. The method of claim 6, wherein the detecting step includes a nucleic acid amplification step.

9. The method of claim 6, wherein the detecting step includes a polymerase chain reaction step.

10. The method of claim 6, wherein said detecting step further comprises detecting whether said subject is homozygous for said mutation.

11. A method of screening a human male subject for a genetic predisposition for increased serum PSA levels, comprising:
    detecting the presence or absence of a T/C mutation wherein said mutation is at position −5412 in the promoter of the prostate specific antigen (PSA) gene in a biological sample collected from said subject, said sample comprising DNA containing said promoter of the PSA gene; and
    determining that the subject is at an increased risk of a genetic predisposition for increased serum PSA levels if a C is present at nucleotide position −5412 of the promoter of the PSA gene.

12. The method of claim 11, wherein the detecting step includes a probe hybridization step.

13. The method of claim 11, wherein the detecting step includes a nucleic acid amplification step.

14. The method of claim 11, wherein the detecting step includes a polymerase chain reaction step.

15. The method of claim 11, wherein said detecting step further comprises detecting whether said subject is homozygous for said mutation.

16. A method for identifying a human male subject having an increased risk for having increased serum prostate specific antigen (PSA) levels, comprising:

obtaining a sample comprising DNA from the subject, wherein said DNA contains a promoter of the PSA gene, determining the nucleotide present at nucleotide position −5412 of said promoter of the PSA gene, and determining that said subject has increased risk for having increased serum PSA levels if a C is present at nucleotide position −5412 of the promoter sequence of the PSA gene.

17. The method of claim 16, wherein the detecting step includes a probe hybridization step.

18. The method of claim 16, wherein the detecting step includes a nucleic acid amplification step.

19. The method of claim 16, wherein the detecting step includes a polymerase chain reaction step.

20. The method of claim 16, wherein said detecting step further comprises detecting whether said subject is homozygous for said mutation.

21. A method of screening a human male subject for a genetic predisposition for increased serum PSA levels, comprising:

detecting the presence or absence of a T/G mutation wherein said mutation is at position −5429 in the promoter of the prostate specific antigen (PSA) gene in a biological sample collected from said subject, said sample comprising DNA containing said promoter of the PSA gene; and determining that the subject is at an increased risk of a genetic predisposition for increased serum PSA levels if a G is present at nucleotide position −5429 of the promoter of the PSA gene.

22. The method of claim 21, wherein the detecting step includes a probe hybridization step.

23. The method of claim 21, wherein the detecting step includes a nucleic acid amplification step.

24. The method of claim 21, wherein the detecting step includes a polymerase chain reaction step.

25. The method of claim 21, wherein said detecting step further comprises detecting whether said subject is homozygous for said mutation.

26. A method for identifying a human male subject having an increased risk for having increased serum prostate specific antigen (PSA) levels, comprising:

obtaining a sample comprising DNA from the subject, wherein said DNA contains a promoter of the PSA gene, determining the nucleotide present at nucleotide position −5429 of said promoter of the PSA gene, and determining that said subject has increased risk for having increased serum PSA levels if a G is present at nucleotide position −5429 of the promoter sequence of the PSA gene.

27. The method of claim 26, wherein the detecting step includes a probe hybridization step.

28. The method of claim 26, wherein the detecting step includes a nucleic acid amplification step.

29. The method of claim 26, wherein the detecting step includes a polymerase chain reaction step.

30. The method of claim 26, wherein said detecting step further comprises detecting whether said subject is homozygous for said mutation.

* * * * *